United States Patent
Morris (10) Patent No.: US 9,091,633 B2
(45) Date of Patent: Jul. 28, 2015

(54) APPARATUS AND METHOD FOR LOCATING THE CENTRE OF A BEAM PROFILE

(75) Inventor: Stephen Morris, Shrewsbury (GB)

(73) Assignee: Nightingale—EOS Ltd., Wrexham (GB)

( * ) Notice: Subject to any disclaimer, the term of this patent is extended or adjusted under 35 U.S.C. 154(b) by 218 days.

(21) Appl. No.: 13/699,886

(22) PCT Filed: May 26, 2011

(86) PCT No.: PCT/GB2011/000806
§ 371 (c)(1),
(2), (4) Date: Nov. 26, 2012

(87) PCT Pub. No.: WO2011/148138
PCT Pub. Date: Dec. 1, 2011

(65) Prior Publication Data
US 2013/0063719 A1    Mar. 14, 2013

(30) Foreign Application Priority Data

May 28, 2010    (GB) .................................. 1009040.5

(51) Int. Cl.
G01J 1/02        (2006.01)
G01N 21/21       (2006.01)
G01J 1/42        (2006.01)

(52) U.S. Cl.
CPC ............. *G01N 21/211* (2013.01); *G01J 1/4257* (2013.01)

(58) Field of Classification Search
CPC ......... G01N 21/211; G01J 1/02; G01J 1/4257
USPC ....................................................... 356/121
See application file for complete search history.

(56) References Cited

U.S. PATENT DOCUMENTS

| 4,999,014 A | 3/1991 | Gold et al. |
| 5,042,951 A | 8/1991 | Gold et al. |

(Continued)

FOREIGN PATENT DOCUMENTS

| DE | 102004016322 A1 | 10/2004 |
| JP | S62267606 A | 11/1987 |

(Continued)

OTHER PUBLICATIONS

Fan Hua et al., "Novel Optical Sensor for precise Tilt Angle Measurement", Control, Automation, Robotics and Vision, 2006. ICARCV '06. 9th International Conference ON, IEEE, PI, Dec. 5, 2006, p. 104.

(Continued)

*Primary Examiner* — Roy M Punnoose
(74) *Attorney, Agent, or Firm* — Morgan, Lewis & Bockius LLP (57) ABSTRACT

A method for locating the center of a beam profile, comprises the steps of: providing a beam profile; selecting one or more strips through the beam profile; identifying distinct regions of intensity along the one or more strips and labelling them consistently; calculating a combined average intensity for each labelled region, using data from the one or more strips; plotting the average intensity against the labelled regions and comparing the results with a plot of the actual intensity obtained by taking a cross-section through the center of at least one of the one or more strips; and optimizing the location of the center of at least one of the one or more strips so as to obtain the best fit between the average intensity plot and the actual intensity plot to thereby identify the center of the beam profile.

19 Claims, 4 Drawing Sheets

(56) References Cited

U.S. PATENT DOCUMENTS

| | | | |
|---|---|---|---|
| 5,136,149 | A | 8/1992 | Fujiwara et al. |
| 6,677,565 | B1 | 1/2004 | Wahl et al. |
| 6,744,510 | B2 | 6/2004 | Gweon et al. |
| 7,081,957 | B2 | 7/2006 | Norton |
| 7,116,610 | B2 | 10/2006 | Ninomiya et al. |
| 7,230,705 | B1 | 6/2007 | Yang et al. |
| 7,236,680 | B1 | 6/2007 | Jordan |
| 7,327,452 | B2 | 2/2008 | Frank et al. |
| 7,583,388 | B2 | 9/2009 | Seko et al. |
| 7,978,932 | B2 | 7/2011 | Vercauteren et al. |
| 8,760,756 | B2 | 6/2014 | Price et al. |
| 2005/0083537 | A1 | 4/2005 | Kuchel |
| 2006/0039643 | A1 | 2/2006 | Saaski |
| 2007/0077009 | A1 | 4/2007 | Luyssaert et al. |
| 2010/0171965 | A1* | 7/2010 | Morris .......................... 356/612 |
| 2013/0070245 | A1* | 3/2013 | Morris .......................... 356/369 |

FOREIGN PATENT DOCUMENTS

| | | |
|---|---|---|
| JP | S6358119 A | 3/1988 |
| JP | 3326931 B2 | 9/2002 |
| JP | 2006260487 A | 9/2006 |
| WO | WO-2008119982 A1 | 10/2008 |
| WO | WO-2008119984 A1 | 10/2008 |

OTHER PUBLICATIONS

Groenewald B. et al., "Substrate Curvature Measurement System", Dielectric Materials, Measurements and Applications Conference, Publ. No. 473, pp. 458-463 (IEE 2000).

International Search Report issued for International Application No. PCT/GB2011/000806 on Oct. 4, 2011 and mailed on Oct. 12, 2011.

International Search Report issued for International Application No. PCT/GB2011/000811 on Nov. 4, 2011 and mailed on Nov. 15, 2011.

* cited by examiner

APPARATUS AND METHOD FOR LOCATING THE CENTRE OF A BEAM PROFILE

CROSS-REFERENCE TO RELATED APPLICATIONS

This application is a U.S. National Phase Application of PCT/GB2011/000806, filed May 26, 2011, which claims priority to and the benefit of United Kingdom Patent Application No. 1009040.5, filed May 28, 2010. The entire disclosure of each of these applications is incorporated by reference herein.

FIELD OF THE INVENTION

This invention relates to an apparatus and method for locating the centre of a beam profile. Furthermore, the invention relates to an apparatus and method for determining the orientation of a sample in an optical measurement apparatus, by location of the centre of a beam profile.

BACKGROUND TO THE INVENTION

Beam Profile Reflectometry (BPR) and Beam Profile Ellipsometry (BPE), described in U.S. Pat. Nos. 4,999,014 and 5,042,951 respectively, are established methods for measuring the thicknesses of thin films and coatings deposited upon flat substrates. Each of these techniques makes use of data contained in the cross-sectional profile of a laser beam which has been reflected from the sample under test. As described in each of these patents, each technique relies on the sample under test being (a) perfectly flat and (b) aligned so that an incident probe beam is focused substantially normal to the surface of the sample.

In practice, known implementations of BPR rely on a very high degree of accuracy in achieving this alignment, since only when the alignment is perfect are the beam profiles obtained symmetrical, and this in turn is an assumption made in the subsequent analysis. To this end, the present inventor has devised a sophisticated five-axis stage arrangement (described in WO2008/119982) which, when used in combination with optical feedback from a BPR system, can be used to align a sample (including samples with complex shapes) to an arbitrarily high degree of accuracy.

However, the requirement for this alignment (whether achieved statically for flat samples by very accurate construction of supporting hardware, or dynamically for curved surfaces using a stage such as that referred to above) introduces significant cost and complexity into a BPR or BPE system.

More specifically, BPR and BPE tend to rely on the ability to fit a calculated optical interference fringe pattern to an experimentally-measured interference fringe pattern obtained from appropriate optical hardware. Where the sample being measured is misaligned, an essential part of this process is to be able to ascertain the nature of the misalignment (i.e. the actual orientation of the sample), which in practice means locating the centre of the beam profile, which, in the case of BPR and BPE comprises an interference fringe pattern. As disclosed in the Applicant's earlier application WO2008/119982, misalignment of the sample causes the image of the reflected laser beam's profile, after it has been refracted through the main objective lens, to become asymmetrical with more light being reflected in the direction towards which the sample is tilted. In that application, however, no quantitative estimate of the amount of misalignment was made, it being sufficient to know in which direction a motorised axis needed to be moved while an optical feedback loop was provided to monitor the changing alignment state.

In addition to the effect of misalignment in the sample's orientation, where the measured data is collected using a coherent laser beam as the light source, the interference fringe pattern is typically contaminated by a large amount of so-called 'speckle' noise caused by interference between specularly-reflected light from the sample and scattered light from surface defects and/or dust particles on the system's optical components.

The Applicants have found that, despite the existence of many algorithms for filtering noisy data and locating the centre of an interference pattern, none of them have proved suitable for the peculiar characteristics of BPR and BPE fringe patterns where (a) the fringe spacing is not regular but becomes much 'denser' as one goes from the centre to edge of the pattern, with the rate-of-change depending on the sample refractive index which is not known beforehand, and (b) misaligned fringe patterns do not consist of perfect concentric circles but of 'distorted' circles which are also unevenly illuminated.

It is therefore an aim of the present invention to address these issues in order both to smooth out a noisy interference pattern and to accurately locate its centre.

Figure 1:
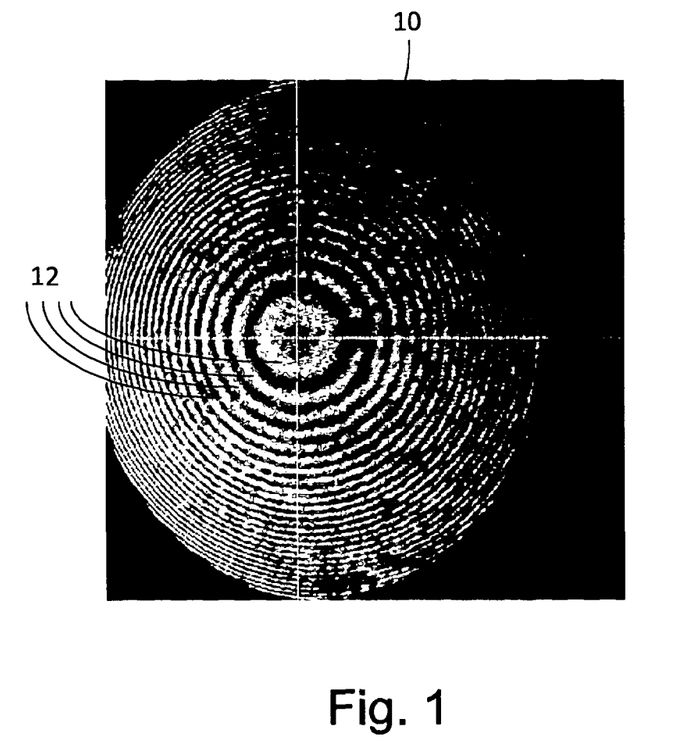
FIG. 1 illustrates a typical BPR beam profile in the form of an interference fringe pattern.

By way of further background, FIG. 1 illustrates a typical BPR beam profile in the form of an interference fringe pattern 10 for a misaligned sample. As can be seen, this pattern 10 comprises a set of nominally concentric fringes 12 (however, such fringes are not always present in the interference pattern, for example, where very thin coatings are provided on the sample). It will also be clear from FIG. 1 that the interference pattern 10 comprises numerous 'asymmetries'. In particular, an essentially random laser speckle pattern is overlaid on the fringe pattern itself, and can cause intensity variations of ~10% of the fringe intensity, sometimes more. Even for a well-aligned sample, if the light source is plane-polarised then the fringes 12 are not perfectly circular: they have reflection symmetry (in the case of a horizontal or vertical polarisation, the symmetry is top/bottom and left/right) but not rotation symmetry. Also, when there are multiple fringes 12, the fringe 12 spacing decreases rapidly as one goes from the centre of the pattern 10 to the edge, but the rate at which this happens depends upon the very properties of the sample that one is usually trying to measure with the BPR apparatus (for example, the thickness of one or more thin film coatings on the sample). This last feature, in particular, rules out the standard method of filtering an image for speckle noise, namely to produce a two-dimensional Fourier transform and then remove the high-frequency components, because the level of filtering necessary to smooth the widest, innermost fringes 12 is likely to obliterate the outermost fringes 12 altogether. Furthermore, when the sample is misaligned, the fringes 12 become 'compressed' in the direction of the misalignment and 'stretched' elsewhere, so that even the top/bottom and left/right reflection symmetry is lost and the illumination is such that neither the brightest part of the image, nor its centroid (which can be thought of as the 'centre of gravity' of the image where brightness corresponds to mass) correspond to the centre of the fringe pattern 10.

It is therefore an aim of the present invention to provide an apparatus and method that addresses at least some of the afore-mentioned problems.

SUMMARY OF THE INVENTION

According to a first aspect of the present invention there is provided a method for locating the centre of a beam profile, comprising the steps of:

providing a beam profile;

selecting one or more strips through the beam profile;

identifying distinct regions of intensity along the one or more strips and labelling them consistently;

calculating a combined average intensity for each labelled region, using data from he one or more strips;

plotting the average intensity against the labelled regions and comparing the results with a plot of the actual intensity obtained by taking a cross-section through the centre of at least one of the one or more strips; and optimising the location of the centre of at least one of the one or more strips so as to obtain the best fit between the average intensity plot and the actual intensity plot to thereby identify the centre of the beam profile.

Embodiments of the invention effectively provide a method which can be used to accurately locate the centre of a beam profile even when the profile is asymmetrical. This information may be used to determine the orientation of the sample generating the beam profile. Conveniently, embodiments of the present invention can help to smooth out a noisy beam profile, for example, to remove speckle interference. In addition, the present invention can determine the centre of a beam profile for a sample having unknown physical characteristics (for example, an unknown surface structure or coating), because the method does not, at any point, require any assumptions about the sample or the surface reflectance itself.

The beam profile may be obtained from light reflected from or transmitted through a sample.

The beam profile may be constituted by an intensity pattern, a reflectance pattern or a transmittance pattern.

The actual intensity (i.e. raw data) may be obtained by taking cross-section through the centre of each of the one or more strips.

The location of the centre of each of the one or more strips may be optimised so as to obtain the best fit between the average intensity plot and the actual intensity plot.

The beam profile may comprise an interference pattern. The interference pattern may comprise one or more fringes. However, in other embodiments (such as when analysing light reflected from a bare substrate), no interference pattern, and no fringes, may be present in the beam profile.

The beam profile may have intensity variations. The intensity variations may have roughly circular symmetry, such as will be the case when the beam profile is obtained using a Gaussian laser beam source.

As the aim is to identify the centre of the beam profile, the one or more strips are ideally taken through a point in the beam profile that is suspected to constitute the centre of the beam profile.

In certain embodiments, a first strip and a second strip may be taken through the bears profile. The first and second strips may be angularly off-set, The first strip may be taken vertically through the beam profile. The second strip may be taken horizontally through the beam profile.

Where more that one strip is employed, each strip may be angularly off-set by a pre determined amount, for example, 45°, 60° or 90°. The amount of off-set may be determined by the nature of symmetry of the beam profile. For example, a beam profile having top/bottom and left/right reflection symmetry may be most efficiently analysed by the employing first and second strips that are angularly off-set by 90°.

In certain embodiments of the invention three or more strips may be selected and employed throughout the method. The third (or further) strips may be angularly off-set by the same or a different amount with respect to the first and/or second strips.

The step of identifying distinct regions of intensity and labelling them consistently may comprise identifying common regions and/or portions of continuous regions extending from one strip to another strip.

The step of identifying distinct regions of intensity and labelling them consistently may comprise associating one pixel in the beam profile with light reflected at normal incidence from the sample and each of the other pixels in the beam profile with an angle $\Theta$ describing the angle of a light ray which arrives at that pixel, relative to the normal. This association may be performed by a ray-tracing technique.

The ray-tracing technique may comprise determining the path of a light ray emerging from a light source and being reflected from the sample to a detector configured to provide the beam profile. The light source may be constituted by a laser. The detector may comprise a plurality of pixels such as those provided in a CMOS or CCD array.

The ray-tracing technique may further comprise determining the path of the light ray through one or more optical elements. The optical elements may be constituted by a lens (e.g. an objective lens and/or a relay lens), a beamsplitter, a retarder, a polarizer or an analyzer.

In particular embodiments, the ray-tracing may be performed in reverse (e.g. tracing the path that a light ray would take, starting from a pixel in the detector, back through the optical system to a point in the light source).

In particular embodiments, the ray-tracing technique may comprise one or more of the features described in the Applicants co-pending UK patent application, Attorney file reference PB141826GB. As explained in that patent application, using 'time reversal' in the ray-tracing technique is advantageous in that it can substantially reduce the size of the calculation that must be carried out and therefore it can be used to simplify and accelerate the procedure. The reason that this approach can substantially reduce the size of the calculation will become apparent from consideration of the following. It will be understood that parameters describing the orientation of a sample are continuous in nature (i.e. the surface of the sample is continuous so light can reflect from it at any location) but the light-sensitive elements of a physical detector are discrete (i.e. the detector is composed of a plurality of individual detector elements or pixels). If a ray is considered to start from a certain location (x, y) within a source beam and is followed through an optical system to a detector at a location (x', y'), it may reach the detector at a position close to an individual detector element's centre, at its edge or even between elements. In order to calculate correctly the final intensity value recorded by the detector element at (or closest to) (x', y'), it is necessary to know not only the amplitude and phase of the light ray that originated at (x, y) but also the amplitude and phase of all the other rays from the source beam that eventually arrive at the same detector element. When the rays themselves are of course not discrete but form part of a continuous light beam, this becomes a complicated calculation, involving a time-consuming interpolation step similar to that described in another of the Applicant's earlier patent applications, published as WO2008/119984. It is therefore possible to reduce the size of the calculation by starting the ray-tracing technique from the detector (in particular, from an individual detector pixel) since only those rays that will influence the detector response need be considered.

The ray-tracing technique may comprise ray-tracing a light path starting from a detector, at the location of a given detector element (e.g. pixel), and following the ray backwards through an optical measurement apparatus to a point in its source. The technique may further comprise obtaining the amplitude of light from the source at said point. The technique may then comprise using the amplitude and the transmission and/or reflection characteristics of the light path to determine the intensity of the light when it reaches the detector element.

The amplitude of light from the light source may be determined from an analytical function or a lookup table and/or these may be calibrated according to intensities measured from a sample with known reflectance and/or orientation.

The method may further comprise the step of combining the intensities of each light ray at the detector element to obtain the total intensity expected.

The method may further comprise repeating the above for a plurality of given detector elements. The method may comprise repeating the above for every given detector element so as to calculate a complete detector response. Alternatively, the above steps may be repeated for a subset of given detector elements—for example, to calculate the response from an array of horizontally-spaced and/or vertically-spaced given detector elements.

The method may comprise the step of generating an expected beam profile in the form of a beam profile wherein the value obtained at each given detector element corresponds to the reflectance coefficient of the sample for light that arrives at each given detector element. The beam profile may be obtained by performing the above described ray-tracing technique for a sample of known orientation and setting the reflectance of the sample to 100% (rather than whatever value would be obtained from the sample coating), and then dividing the measured intensity pattern by the calculated 100% reflectance.

The one or more strips may have a width that is chosen so as to include enough pixels in each region to average out the speckle noise while spanning a small enough range of angles that closely-spaced fringes do not merge into one. In addition, the width may be chosen to preserve any asymmetry that might be present in the beam profile. For example, asymmetry usually exists in BPR and BPE beam profiles between the horizontal and vertical directions, one of which usually represents the reflectance of s-polarised light and the other the reflectance of p-polarised light.

It will be noted that where the beam profile comprises an interference fringe pattern, a strip through the approximate centre of the pattern may contain distinct regions of intensity that form either annuli or arcs. The asymmetry described above in relation to BPR and BPE beam profiles is usually found to be negligible at small angles of incidence and to increase towards higher angles of incidence so that the fact that the regions are annuli, encompassing a whole range of azimuths, at small angles of incidence does not matter so long as the strip is sufficiently narrow that the annuli have become arcs by the time the differences between s and p reflectance are significant.

The step of plotting the average intensity against the labelled regions may comprise fitting a curve to the individual data points. The curve may be fitted to the data using any appropriate technique.

The method may further comprise a calibration step. The calibration step may comprise determining the intensity characteristics of a light source and/or the alignment of optical elements within an optical measurement apparatus configured to provide the beam profile, in order to facilitate the identification of each pixel in the beam profile with a particular angle-of-reflection $\Theta$ and to enable the calculation of the source intensity at each pixel. This calibration step may involve examining the beam profiles obtained from one or more samples of known surface characteristics and/or orientations, for example flat silicon coupons bearing $SiO_2$ films of known thickness. Additionally or alternatively, the calibration step may comprise the step of determining the diameter of the beam and/or determining the numerical aperture and/or focal point of the objective lens, so as to facilitate the association of each pixel in the beam profile with a particular angle-of-reflection $\Theta$.

The method may be configured for locating the centre of a beam profile during Beam Profile Reflectometry (BPR), Beam Profile Ellipsometry (BPE), Spectrophotometry, Spectroscopic Ellipsometry or an alternative optical measurement technique.

According to a second aspect of the present invention there is provided a method of determining the orientation of a sample in an optical measurement apparatus, comprising the steps of:
  locating the centre of a beam profile obtained from the sample, using the method according to the first aspect of the invention; and
  relating the centre of the beam profile to the angle of a light ray normally incident on the sample, relative to an optical axis of the optical measurement apparatus, to thereby establish the angle of the sample relative to the optical axis.

The step of relating the centre of the beam profile to the angle of the light ray normally incident on the sample may comprise mapping the centre of the beam profile from a beam profile co-ordinate system to a co-ordinate system associated with the optical measurement apparatus, such as that associated with an objective lens focussing light on or through the sample in order to generate the beam profile.

The step of relating the centre of the beam profile to the angle of the light ray normally incident on the sample may comprise a ray-tracing technique such as that described above. In particular, ray-tracing may be used to associate each pixel in a detector (or each pixel in the beam profile) with a particular angle of incidence relative to the optical axis. In other embodiments, the ray-tracing may be used to associate the centre of the beam profile with a particular angle of incidence relative to the optical axis.

A particular embodiment of the second aspect of the invention comprises:
  providing a beam profile comprising a plurality of pixels;
  selecting a given location within the beam profile as a first estimate of the centre of the beam profile;
  selecting a strip of a given width, centred on the given location;
  generating a set of labelled regions within the strip such that, if the given location were in the centre of the beam profile, then all pixels in each region would derive from light reflected from the sample at approximately equal angles-of-reflection;
  plotting the average intensity within each region as a function of the approximately equal angles-of-reflection, to obtain a plot which, if the given location were in the centre of the beam profile, would correspond to a plot of intensity against angle-of-reflection;
  obtaining a plot of the intensity variation along the centre of the strip (which by definition is a plot of intensity against angle-of-reflection);
  comparing the average intensity plot with the intensity variation plot such that the given location were in the centre of the beam profile, the plots would have a similar form;
  iteratively improving the estimate of the given location until the best attainable match between the two plots is obtained and therefore the centre of the beam profile is determined; and relating the centre of the beam profile to the angle of a light ray normally incident on the sample, relative to an optical axis of the optical measurement apparatus, to thereby establish the angle of the sample relative to the optical axis.

It will be noted that, in accordance with the second aspect of the invention, i is possible to determine the orientation of the sample by simply analysing the beam profile, as described above. Accordingly, with this aspect of the invention there is no need to determine the details of the sample composition (for example, the thickness and/or refractive index of one or more coatings on the sample) in order to establish its orientation.

It will be understood that because the method makes no assumptions about the nature of the sample, it has applications much wider than just making coating thickness measurements using BPR or BPE. On the contrary, the present method can be used to measure the orientation of any sample (i.e. any tilted reflective surface), likewise, the present method can be carried out without utilising any information about the amplitude distribution of the source. However, if such information is available and is used to divide both intensity plots (i.e. that obtained from averaging over the labelled regions, and that obtained from a simple cross-section along the centre of the strip), then when the correct alignment is obtained both these plots will be symmetrical, whereas away from alignment they are asymmetrical, which further enhances the sensitivity of the technique to find the true centre.

The method can be carried out using a single such strip, but using more than one strip (in the preferred embodiment, two) further enhances the sensitivity.

According to a third aspect of the present invention there is provided a carrier medium carrying computer readable program code configured to cause a computer to carry out the method according to the first and/or second aspect of the invention.

According to a fourth aspect of the present invention there is provided a device comprising:
a program memory containing computer readable instructions; and
a processor configured to read and execute instructions stored in said program memory;
wherein said processor readable instructions comprise instructions configured to control said device to carry out the method according to the first and/or second aspect of the invention.

According to a fifth aspect of the present invention there is provided an apparatus for locating the centre of a beam profile, comprising:
an optical measurement system configured to generate a beam profile for a sample concerned; and
a device according to the fourth aspect of the invention.

The optional features described above in relation to the first aspect of the invention, apply equally to the second, third, fourth and fifth aspects of the invention, as appropriate.

The method and apparatus of the present invention may be employed in various applications and in a wide range of industries. Particularly, but not exclusively, the method and apparatus may find application in coating thickness metrology, for example, in semiconductor or medical device manufacturing,

BRIEF DESCRIPTION OF THE DRAWINGS

Embodiments of the invention will now be described, as examples only, with reference to the accompanying drawings, in which.

DETAILED DESCRIPTION OF CERTAIN EMBODIMENTS

As explained above, FIG. 1 shows a typical BPR beam profile in the form of an interference pattern 10 having multiple, generally concentric ring fringes 12, taken from a sample which was misaligned with respect to the focal plane of the optical apparatus that generated the beam profile. Due to a combination of the speckle noise in the interference pattern 10 and the fact that the fringes 12 are closer together at the left-hand side of the image than they are at the right-hand side of the image, it is not possible to accurately determine where the centre of the beam profile is using standard techniques. However, as will be described in detail below, the location of the centre of the beam profile can be accurately determined using embodiments of the present invention.

Figure 2:
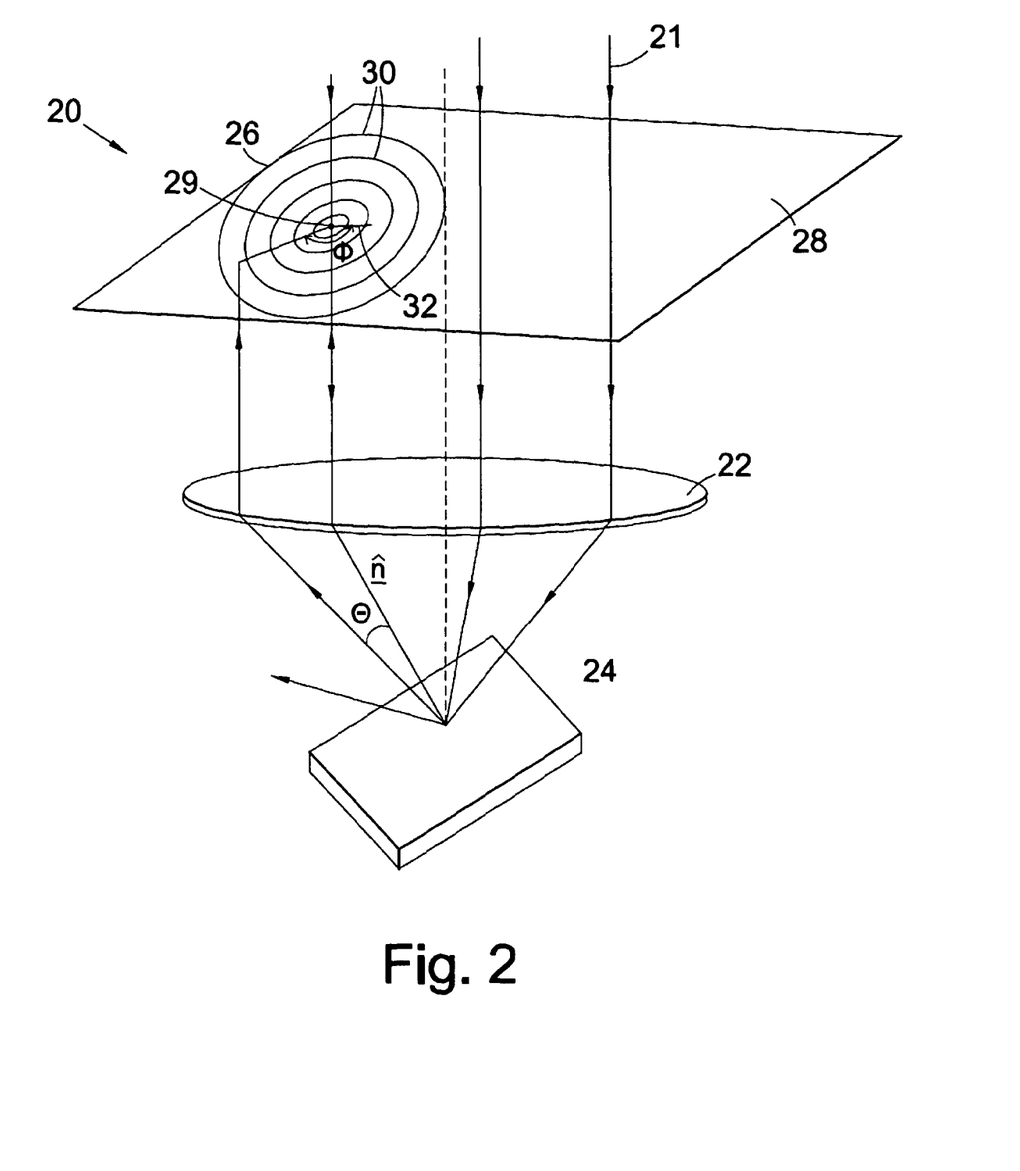
FIG. 2 illustrates a method and apparatus according to embodiments of the present invention.

FIG. 2 shows a method and apparatus according to a first embodiment of the present invention. More specifically, FIG. 2 shows a portion of a BPR measurement system 20 in which light rays 21 from a laser source (not shown) is directed (via a beamsplitter, not shown) through an objective lens 22, to focus on a misaligned sample 24 (having a thin film coating thereon) and is then re-collimated by the objective lens 22 to form a beam profile in the form of an interference fringe pattern 26 in a Fourier plane 28. It will be understood that, in practice, the Fourier plane will be (re-)imaged on a detector (not shown), and further optical components (such as a retarder, polariser and relay lens) may be provided between the objective lens 22 and the detector, in a similar manner to the apparatus shown in FIG. 2 of the Applicants co-pending UK patent application, Attorney file reference PB141826GB. It will also be understood that each point on the Fourier plane 2 corresponds to a particular angle of travel of light reflected from the sample 24.

As the sample 24 is misaligned with the focal plane of the objective lens 22, the interference fringe pattern 26 is offset from the optical axis of the objective lens 22, as illustrated. It will also be clear that light rays 21 incident normal to the sample 24 (i.e. along a normal unit vector $\hat{n}$) will be reflected back along the same path and that the point where this path intersects the Fourier plane 28, defines the centre 29 of the fringe pattern 26. Light rays 21 arriving at the sample 24 at any other angle will be reflected back at an angle $\Theta$ relative to the normal $\hat{n}$ and such rays will interfere at the Fourier plane 28 to form generally circular fringes 30 extending outwardly from the centre of the fringe pattern 26, although the precise shape of these fringes 30 will be determined by the tilt of the sample 24.

In order to determine the centre 29 of the fringe pattern 26 (and thereby enable the misalignment ($\theta_x$, $\theta_y$) of the sample 24 to be determined), we can use a reverse ray-tracing technique similar to that described in the Applicants co-pending UK patent application, Attorney file reference PB141826GB. Accordingly, we can associate one pixel in the beam profile 26 with the concept of normal incidence (i.e. we can consider the one pixel to be at the centre of the beam profile) and we can associate each of the other pixels in the beam profile 26 with the angle $\Theta$ describing the angle of the light ray which arrives at that pixel relative to the normal unit vector n̂. It is therefore possible to think of the angle $\Theta$ as forming one half of a ($\Theta$, $\Phi$) polar co-ordinate system describing each pixel in the beam profile 26 according to its angle and azimuth relative to the normal unit vector and some given reference direction, such as the horizontal axis 32 of the Fourier plane 28.

Figure 3A:
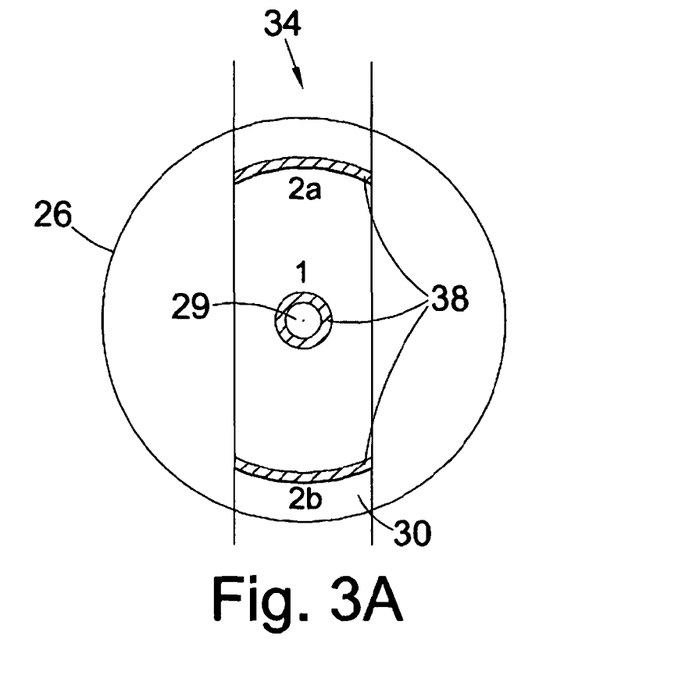
FIG. 3A illustrates the selection of a vertical strip through the beam profile, in accordance with an embodiment of the present invention.
Figure 3B:
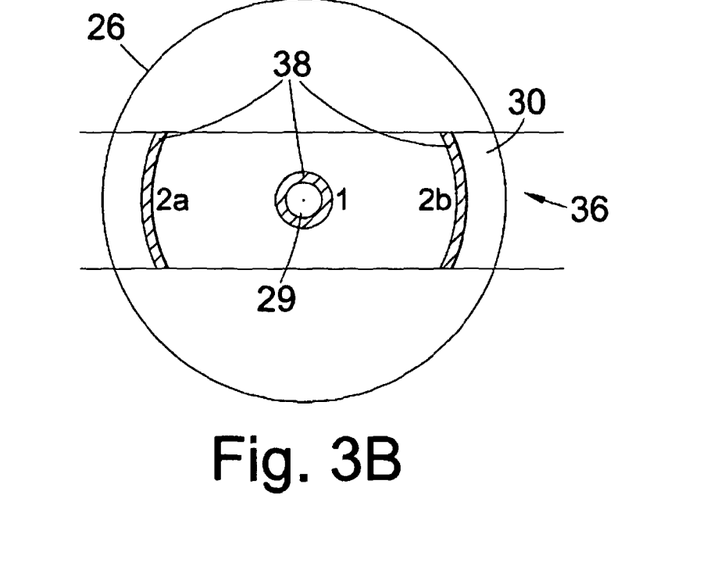
FIG. 3B illustrates the selection of a horizontal strip through the beam profile, in accordance with an embodiment of the present invention.

In this particular embodiment, we now take a pair of vertical 34 and horizontal 36 strips through the beam profile 26, as illustrated respectively in FIGS. 3A and 3B. Within each strip 34, 36, we can identify regions (or contours) 38 of equal $\Theta$ which, depending on the width of the strip 34, 36 and the distance of the region 38 from the centre 29 may comprise either annuli (such as those labelled '1') or arcs (such as those labelled '2'). As long as the centre of each of the strips 34, 36 is aligned with the centre 29 of the fringe pattern 26, calculating the average value of all the pixels within one of these combined regions (e.g. averaging all of the pixels in regions 1 from both strips 34, 36 or averaging all of the pixels in regions 2 from both strips 34, 36) provides us with a way of integrating along each of the individual fringes 30 and so allows us to obtaining an average intensity value for each angle $\Theta$.

Figure 4A:
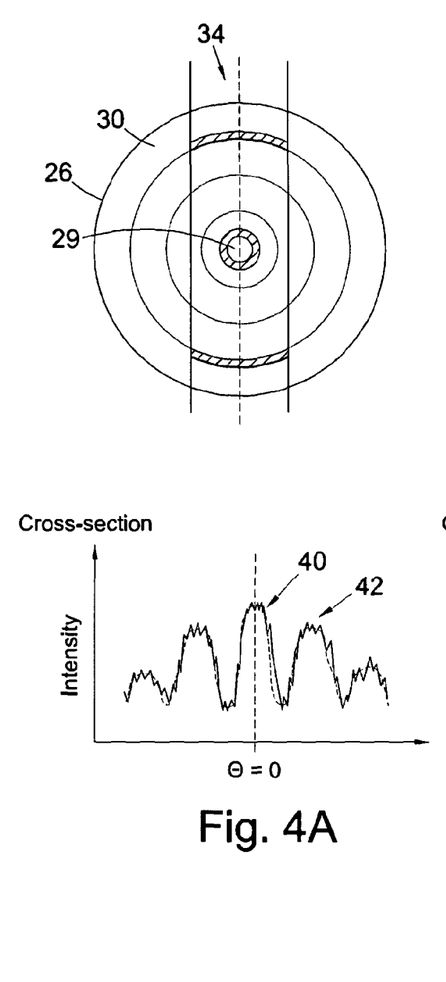
FIG. 4A illustrates a plot of the average intensity against angle of incidence compared to a plot of the intensity of the raw data obtained by taking a cross-section through the centre of the vertical strip shown above, where the strip is correctly centred in the beam profile, in accordance with an embodiment of the present invention.

This allows us to plot a graph of the averaged intensity as a function of the angle $\Theta$, as shown in FIG. 4k If we then fit a curve 40 to the averaged intensity values, for example by using a Known cubic spline technique, and also plot the actual intensity values 42 obtained by taking a cross-section through the centre of one of the first or second strips 34, 36 we can see that the results closely match where the fringe centre 29 has been correctly assumed at the centre of vertical strip 34, as also illustrated in FIG. 4A. We can also see from the graph of FIG. 4A that the method described above helps to produce smoothed curves representing the fringes 30 where (a) the (speckle) noise in the beam profile 26 has been very effectively filtered out and (b) the fine structure of the fringe pattern is preserved even when the fringes 30 are very close together.

Figure 4B:
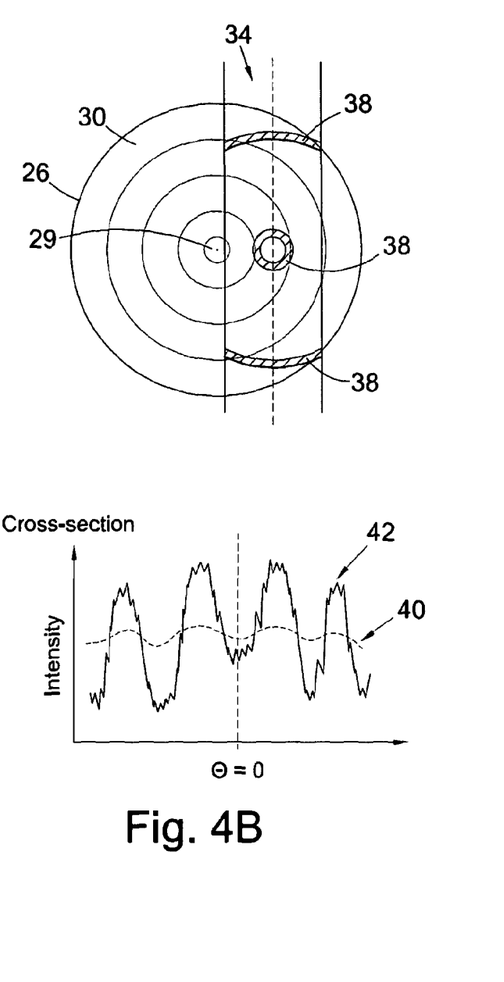
FIG. 4B illustrates a plot of the average intensity against angle of incidence compared to a plot of the intensity of the raw data obtained by taking a cross-section through the centre of the vertical strip shown above, where the strip is not centred in the beam profile, in accordance with an embodiment of the present invention.

However, as shown in FIG. 4B, where the centre of the beam profile 26 has not been correctly assumed and the centre of the vertical (and/or horizontal) strip 34 is not coincident with the centre of the fringe pattern, we will obtain the graph shown in FIG. 4B where the smoothed curve 40 does not fit the raw data 42. It is noted that even when the strip is not centred, the actual intensity plot is still by definition a plot of intensity against angle because each pixel represents a different angle; however, in this case the minimum angle in the plot may not correspond to zero degrees. It will be noted in FIG. 4B that the regions 38 employed to calculate the average intensity actually cut across the true fringe pattern and consequently, the averaging process smears out the underlying intensity variations. However, the fringes in the actual intensity plot are still sharp because there is no smearing caused by averaging, although the fringes will appear wider apart than when the strip goes through the centre.

In view of the above, it will be clear that it necessary to optimise the location of the strip centres so as to obtain the best fit between the smoothed curves and the raw data. This can be done for example by using a nonlinear optimisation technique such as the Levenberg-Marquardt algorithm, treating the x and y co-ordinates of the centre as adjustable parameters.

Once the best fit has been obtained and the true position of the centre 29 of the beam profile 26 determined, it will be possible to use this information to determine the true orientation of the sample 24 by relating the centre of the beam profile 26 to the angle of a light ray normally incident on the sample 24 (relative to an optical axis of the optical measurement apparatus) to thereby establish the angle of the sample 24 relative to the optical axis. In certain embodiments, a calibration step may be employed in order to establish the relationship between the detector pixels and the angle of light arriving at each pixel, relative to the optical axis. It will also be noted that the orientation of the sample can therefore be obtained without any analysis of the fringe pattern as such and therefore without needing to know or make any assumptions about the physical characteristics of the surface of the sample 24.

It will be understood that, in order to achieve the best balance between filtering out the (speckle) noise and preserving the structure of the fringe pattern, it will be necessary to choose with care the width of each strip 34, 36 and the number of regions 38 therewithin. In practice, each region 38 should contain enough pixels to average out the speckle noise, while spanning a small enough range of $\Theta$ that closely-spaced fringes 30 do not become 'washed out' The width of each strip 34 36 must therefore be wide enough to provide the requisite number of pixels in each region 38, while preserving the asymmetry which usually exists in a BPR or BPE pattern (where applicable) between the horizontal and vertical directions, one of which usually represents the reflectance of s-polarised light and the other the reflectance of p-polarised light. The Applicants have empirically determined that for fringe pattern images of ~800×800 pixels, a strip width of ~60 pixels containing 100-200 regions has been found to give good results for most fringe patterns.

Although the above-described embodiment of the present invention has been based on a beam profile 26 comprising an interference fringe pattern, other embodiments have been found just as effective where there is no fringe pattern—for example when looking at light reflected from a bare sample (i.e. a flat substrate).

It will be appreciated by persons skilled in the art that various modifications may be made to the above embodiments without departing from the scope of the present invention. For example, whilst the above discussion has been primarily concerned with locating the centre of a beam profile obtained using the optical measurement techniques of BPR and BPE, the invention is equally applicable to use with other optical measurement techniques.

The invention claimed is:

1. A method for locating the centre of a beam profile, comprising the steps of:
  providing a beam profile;
  selecting one or more strips through the beam profile;
  identifying distinct regions of intensity along the one or more strips and labelling them, wherein the step of identifying distinct regions of intensity and labelling them comprises (i) associating one pixel in the beam profile with light reflected at normal incidence from the sample, (ii) associating other pixels in the beam profile each with an angle $\Theta$ describing the angle of a light ray which arrives at that pixel, relative to the normal, and (iii) identifying regions of equal angle Θ as labelled regions;

calculating an average intensity for each labelled region, using data from the one or more strips;

plotting the average intensity against the labelled regions and comparing the results with a plot of the actual intensity obtained by taking a cross-section through the centre of at least one of the one or more strips; and optimising the location of the centre of at least one of the one or more strips by obtaining the best fit between the average intensity plot and the actual intensity plot to thereby identify the centre of the beam profile.

2. The method according claim 1 wherein a first strip and a second strip is taken through the beam profile, the first and second strips being angularly off-set.

3. The method according to claim 1 wherein the step of identifying distinct regions of intensity and labelling them comprises identifying one of (a) common regions or (b) portions of continuous regions extending from one strip to another strip.

4. The method according to claim 1 wherein the associating is performed by a ray-tracing technique that comprises determining the path of a light ray emerging from a light source and being reflected from the sample to a detector configured to provide the beam profile.

5. The method according to claim 4 further comprising determining the path of the light ray through one or more optical elements.

6. The method according to claim 4 wherein the ray-tracing is performed in reverse and comprises ray-tracing a light path starting from a detector, at the location of a given detector element, and following the ray backwards through an optical measurement apparatus to a point in its source.

7. The method according to claim 6 further comprising obtaining the amplitude of light from the source at said point and using the amplitude and at least one of the transmission or the reflection characteristics of the light path to determine the intensity of the light when it reaches the detector element.

8. The method according to claim 7 further comprising the step of combining the intensities of each light ray at the detector element to obtain the total intensity expected.

9. The method according to claim 1 comprising the step of generating an expected beam profile in the form of a beam profile wherein the value obtained at each given detector element corresponds to the reflectance coefficient of the sample for light that arrives at each given detector element.

10. The method according to claim 9 wherein the beam profile is obtained by performing a ray-tracing technique for a sample of known orientation and setting the reflectance of the sample to 100%, and then dividing the measured intensity pattern by the calculated 100% reflectance.

11. A method of determining the orientation of a sample in an optical measurement apparatus, comprising the steps of:

locating the centre of a beam profile obtained from the sample, using the method according to claim 1; and relating the centre of the beam profile to the angle of a light ray normally incident on the sample, relative to an optical axis of the optical measurement apparatus, to thereby establish the angle of the sample relative to the optical axis.

12. The method according to claim 11 wherein the step of relating the centre of the beam profile to the angle of the light ray normally incident on the sample comprises mapping the centre of the beam profile from a beam profile co-ordinate system to a co-ordinate system associated with the optical measurement apparatus, such as that associated with an objective lens focussing light on or through the sample in order to generate the beam profile.

13. The method according to claim 11 wherein the step of relating the centre of the beam profile to the angle of the light ray normally incident on the sample comprises a ray-tracing technique.

14. The method according to claim 13 wherein ray-tracing is used to associate one of (a) each pixel in a detector or (b) each pixel in the beam profile with a particular corresponding angle of incidence relative to the optical axis.

15. The method according to claim 13 wherein ray-tracing is used to associate the centre of the beam profile with a corresponding angle of incidence relative to the optical axis.

16. The method according to claim 11 comprising:

providing a beam profile comprising a plurality of pixels;

selecting a given location within the beam profile as a first estimate of the centre of the beam profile;

selecting a strip of a given width, centred on the given location;

generating a set of labelled regions within the strip such that, if the given location were in the centre of the beam profile, then all pixels in each region would derive from light reflected from the sample at approximately equal angles-of-reflection;

plotting the average intensity within each region as a function of the approximately equal angles-of-reflection, to obtain a plot which, if the given location were in the centre of the beam profile, would correspond to a plot of intensity against angle-of-reflection;

obtaining a plot of the intensity variation along the centre of the strip;

comparing the average intensity plot with the intensity variation plot such that, if the given location were in the centre of the beam profile, the plots would have a similar form;

iteratively improving the estimate of the given location until the best attainable match between the two plots is obtained and therefore the centre of the beam profile is determined; and relating the centre of the beam profile to the angle of a light ray normally incident on the sample, relative to an optical axis of the optical measurement apparatus, to thereby establish the angle of the sample relative to the optical axis.

17. A non-transitory carrier medium carrying computer readable program code configured to cause a computer to carry out the method according to any preceding claim.

18. A device comprising:

a program memory containing computer readable instructions;

a processor configured to read and execute instructions stored in said program memory; and a non-transitory carrier medium carrying computer readable program code comprising instructions configured to control said device to carry out the method according to claim 1.

19. An apparatus for locating the centre of a beam profile, comprising:

an optical measurement system configured to generate a beam profile for a sample concerned; and a device according to claim 18.

* * * * *